United States Patent [19]
Conrow et al.

[11] 3,985,884
[45] Oct. 12, 1976

[54] COMPLEMENT INHIBITORS
[75] Inventors: Ransom Brown Conrow, Pearl River; Seymour Bernstein, New City, both of N.Y.
[73] Assignee: American Cyanamid Company, Stamford, Conn.
[22] Filed: Dec. 12, 1975
[21] Appl. No.: 640,097

[52] U.S. Cl. .............................. 424/269; 260/308 B
[51] Int. Cl.² ...................................... C07D 249/22
[58] Field of Search ................. 260/308 B; 424/269

[56] References Cited
UNITED STATES PATENTS
2,799,671   7/1957   Gunst .............................. 260/308 B Primary Examiner—Paul M. Coughlan, Jr.
Attorney, Agent, or Firm—Jack W. Richards

[57] ABSTRACT
3,3'-ureylenebis[6-(hydroxysulfo-2H-naphtho[1,2-d]-triazol-2-yl)benzenesulfonic acids] and salts useful as complement inhibitors.

7 Claims, No Drawings

3,985,884

COMPLEMENT INHIBITORS

BACKGROUND OF THE INVENTION

The present invention resides in the concept of certain 3,3'-ureylenebis[6-(hydroxysulfo-2H-naphtho[1,2-d]-triazol-2-yl)benzenesulfonic acids] and their use as inhibitors of the complement system of warm-blooded animals.

The term "complement" refers to a complex group of proteins in body fluids that, working together with antibodies or other factors, play an important role as mediators of immune, allergic, immunochemical and/or immunopathological reactions. The reactions in which complement participates takes place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1$q$, C1$r$ and C1$s$. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.*, 39 935–938 (1968); *Scientific American*, 229, (No. 5), 54–66 (1973); *Medical World News*, Oct. 11, 1974, pp. 53–58; 64–66; *Harvey Lectures*, 66, 75–104 (1972); *The New England Journal of Medicine*, 287, 489–495; 545–549; 592–596; 642–646 (1972); *The Johns Hopkins Med. J.* 128, 57–74 (1971); and *Federation Proceedings*, 32, 134–137 (1973).

The complement system can be considered to consist of three-sub-systems; (1) a recognition unit (C1$q$) which enables it to combine with antibody molecules that have detected a foreign invader; (2) an activation unit (C1$r$, C1$s$, C2, C4, C3), which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflamation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathologic process. The nature of certain of the complement proteins, suggestions regarding the mode of complement binding to biological membranes and the manner in which complement effects membrane damage are discussed in *Annual Review of Biochemistry*, 38, 389 (1969).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)]benzenesulfonic acid tetrasodium salt (chlorazol fast pink), heparin and a sulphated dextran have been reported to have an anticomplementary effect, *British Journal of Experimental Pathology*, 33, 327–339 (1952). The compound 8,8'-[ureylenebis[m-phenylenecarbonylimino(4-methyl-m-phenylene)carbonylimino]]di-1,3,5-naphthalenetrisulfonic acid, hexasodium salt (Suramin Sodium) is described as a competitive inhibitor of the complement system, *Clin. Exp. Immunol.*, 10, 127–138 (1972). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, *Journal of Medicinal Chemistry*, 12, 415–419, 902–905, 1049–1052, 1053–1056 (1969); *Canadian Journal of Biochemistry*, 47, 547–552 (1969); *The Journal of Immunology* 93, 629–640 (1964); *The Journal of Immunology*, 104, 279–288 (1970); *The Journal of Immunology*, 106, 241–245 (1971); and *The Journal of Immunology*, 111, 1061–1066 (1973).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), *The New England Journal of Medicine*, 286, 808–812 (1972); *Allergol, Et. Immunopath, II*, 163–168 (1974); and *J. Allergy Clin. Immunol.*, 53, No. 5, 298–302 (1974).

SUMMARY OF THE INVENTION

It has now been discovered that a representative compound of the invention interacts with the complement reaction sequence, thereby inhibiting complement activity in body fluids.

This invention is particularly concerned with 3,3'-ureylenebis[6-(6,7,8 or 9-hydroxy and sulfo-2H-naphtho[1,2-d]-triazol-2-yl)benzenesulfonic acids] and salts having complement inhibiting activity of the general formula (I):

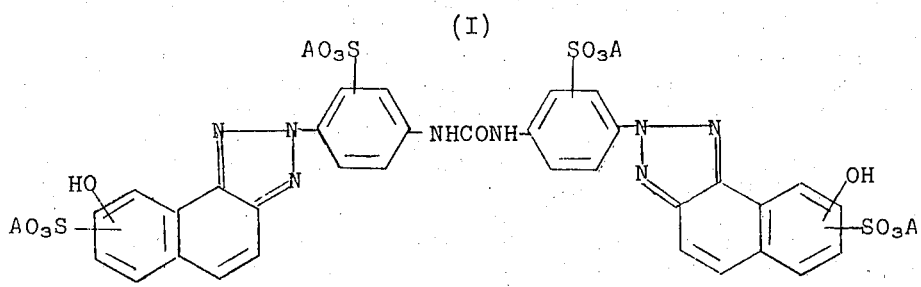

wherein A is H, Na (sodium) or K (potassium), with the proviso that each A is identical in the same compound.

Of particular interest in the above general formula (I) are the group of compounds wherein A is Na and, within this group, the compound of most interest is 3,3'-ureylenebis[6-(9-hydroxy-7-sulfo-2H-naphtho[1,2-d]triazol-2-yl)benzenesulfonic acid] tetrasodium salt having the formula:

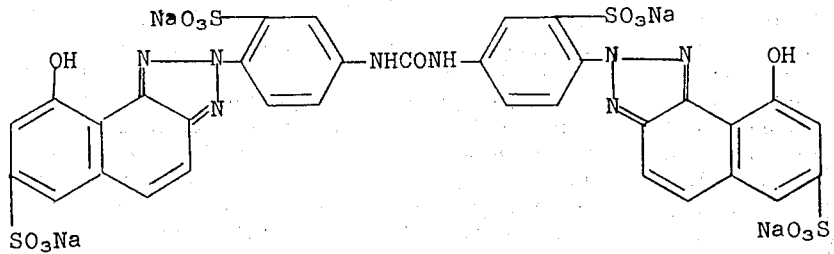

Representative compounds encompassed within this invention include, for example the compound of the formula:

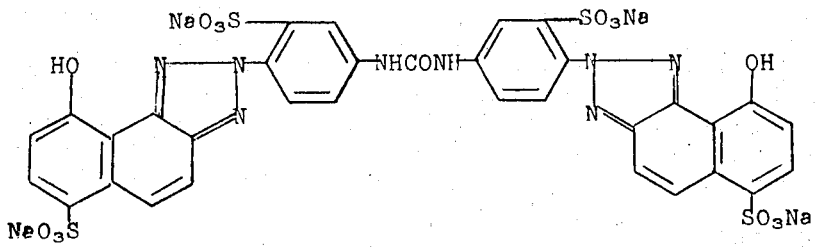

A compound related to those of the present invention, and disclosed as having anticomplementary effect, is the compound 3,3'-ureylenebis[6-(2-amino-8-hydroxy-6-sulfo-1-naphthylazo)benzenesulfonic acid] tetrasodium salt(chlorazol fast pink), *British Journal of Experimental Pathology*, 33, 327–339 (1952).

The compounds of this invention may be prepared, for example, by diazotizing a 3,3'-ureylenebis[(2-amino-8-hydroxy-sulfo-1-naphthylazo)benzenesulfonic acid] tetrasodium salt with nitrous acid followed by treatment with sodium azide. Treatment with acid provide the free sulfonic acids.

This invention is also concerned with a method of inhibiting the complement system in a body fluid, such as blood serum, which comprises subjecting body fluid complement to the action of an effective complement inhibiting amount of a compound encompassed within formula (I) hereinabove. The method of use aspect of this invention is also concerned with a method of inhibiting the complement system in a warm-blooded animal which comprises internally administering to said animal an effective complement inhibiting amount of a compound encompassed within formula (I) hereinabove. Body fluid can include blood, plasma, serum, synovial fluid, cerebrospinal fluid, or pathological accumulations of fluid such as pleural effusion, etc.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemic, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary angioneurotic edema (treated with Suramin Sodium, etc.) and inflammatory states induced by the action of bacterial of lysosomal enzymes on the appropriate complement components as, for example, inflammation following coronary occlusion. They may also be useful in the treatment of transplant rejection.

DETAILED DESCRIPTION OF THE INVENTION

The following examples will serve to illustrate the invention in more detail.

EXAMPLE 1

3,3'-Ureylenebis[6-(9-hydroxy-7-sulfo-2H-naphtho[1,2-d]triazol-2-yl)benzenesulfonic acid] tetrasodium salt To a vigorously stirred solution of 40 g of 3,3'-ureylenebis[6-(2-amino-8-hydroxy-6-sulfo-1-naphthylazo)benzenesulfonic acid] tetrasodium salt in 500 ml of water in a one liter beaker kept at 5° C in an ice bath, is added 160 ml of 88% formic acid which has been pre-cooled in an ice bath. This is followed immediately by a solution of 5.8 g of sodium nitrite in 8 ml of water, added below the surface of the liquid. After stirring for 2-3 minutes, 5.8 g of powdered sodium azide is added portionwise over a period of approximately 5 minutes at a temperature of 6°-7° C, resulting in a vigorous evolution of nitrogen. The mixture is stirred for one hour in an ice bath, then is warmed to room temperature and filtered. The filtrate is heated on a steam bath and 200 g of ammonium acetate is added. The mixture is cooled to room temperature, filtered and the product is washed with a 20% aqueous solution of ammonium acetate to give a dark purple paste. The paste is heated on a steam bath with 40 ml of water and 19.6 g of sodium hydroxide until solution is obtained. A 5.0 g portion of sodium hydrosulfite is added to the strongly basic solution, the mixture is stirred for 2-3 minutes then is made weakly acidic by the addition of 14 ml of acetic acid. The solution of heated to 90° C and filtered through diatomaceous earth. To the filtrate is added 50 g of sodium acetate trihydrate. The solution is cooled to room temperature and the product is separated as a cream precipitate which is washed on the filter with a 20% aqueous solution of sodium acetate trihydrate. The washing is continued by transferring the precipitate to a centrifuge tube; centrifuging and decanting with a total of 100 ml of sodium acetate solution then with ethanol. The product is finally washed on the filter with approximately 300 ml of ethanol and is dried overnight at 110° C over phosphorous pentoxide to obtain 3,3'-ureylenebis[6-(9-hydroxy-7-sulfo-2H-naphtho[1,2-d]triazol-2-yl)benzenesulfonic acid] tetrasodium salt.

Example 2

Preparation of Compressed Tablet

| | mg./tablet |
|---|---|
| 3,3'-Ureylenebis[6-(9-hydroxy-7-sulfo-2H-naphtho[1,2-d]triazol-2-yl)benzenesulfonic acid] tetrasodium salt | 0.5 – 500 |
| Dibasic Calcium Phosphate NF | qs |
| Starch USP | 40 |
| Modified Starch | 10 |
| Magnesium Stearate USP | 1 – 5 |

Example 3

Preparation of Compresses Tablet-Sustained Action

| | mg./tablet |
|---|---|
| 3,3'-Ureylenebis[6-(9-hydroxy-7-sulfo-2H-naphtho[1,2-d]triazol-2-yl)benzenesulfonic acid] tetrasodium salt as aluminum lake, micronized | 0.5 – 500 as acid equivalent |
| Dibasic Calcium Phosphate NF | qs |
| Alginic Acid | 20 |
| Starch USP | 35 |
| Magnesium Stearate USP | 1 – 10 |

Complement inhibitor as sodium salt plus aluminum sulfate yields complement inhibitor plus sodium sulfate. Complement inhibitor content in aluminum lake ranges from 5–30 percent.

Example 4

Preparation of Hard Shell Capsule

| | mg./capsule |
|---|---|
| 3,3'-Ureylenebis[6-(9-hydroxy-7-sulfo-2H-naphtho[1,2-d]triazol-2-yl)benzenesulfonic acid] tetrasodium salt | 0.5 – 500 |
| Lactose, Spray Dried | qs |
| Magnesium Stearate | 1 – 10 |

Example 5

Preparation of Oral Liquid (Syrup)

| | % w/v |
|---|---|
| 3,3'-Ureylenebis[6-(9-hydroxy-7-sulfo-2H-naphtho[1,2-d]triazol-2-yl)benzenesulfonic acid] tetrasodium salt | 0.05 – 5 |
| Liquid Sugar | 75.0 |
| Methyl Paraben USP | 0.18 |
| Propyl Paraben USP | |
| Flavoring Agent | qs |
| Purified Water qs ad | 100.0 |

Example 6

Preparation of Oral Liquid (Elixir)

| | % w/v |
|---|---|
| 3,3'-Ureylenebis[6-(9-hydroxy-7-sulfo-2H-naphtho[1,2-d]triazol-2-yl)benzenesulfonic acid] tetrasodium salt | 0.05 – 5 |
| Alcohol USP | 12.5 |
| Glycerin USP | 45.0 |
| Syrup USP | 20.0 |
| Flavoring Agent | qs |
| Purified Water qs ad | 100.0 |

Example 7

Preparation of Oral Suspension (Syrup)

| | % w/v |
|---|---|
| 3,3'-Ureylenebis[6-(9-hydroxy-7-sulfo-2H-naphtho[1,2-d]triazol-2-yl)benzenesulfonic acid tetrasodium salt as aluminum lake, micronized | 0.05 – 5 (acid equivalent) |
| Polysorbate 80 USP | 01 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

Example 8

Preparation of Injectable Solution

| | % w/v |
|---|---|
| 3,3'-Ureylenebis[6-(9-hydroxy-7-sulfo-2H-naphtho[1,2-d]triazol-2-yl)benzenesulfonic acid] tetrasodium salt | 0.05 – 5 |
| Benzyl alcohol N.F. | 0.09 |
| Water for Injection | 100.0 |

Example 9

| Preparation of Injectable Oil | |
|---|---|
| | % w/v |
| 3,3'-Ureylenebis[6-(9-hydroxy-7-sulfo-2H-naphtho[1,2-d]triazol-2-yl)benzenesulfonic acid] tetrasodium salt | 0.05 – 5 |
| Benzyl Alcohol | 1.5 |
| Sesame Oil qs ad | 100.0 |

Example 10

| Preparation of Injectable Depo Suspension | |
|---|---|
| | % w/v |
| 3,3'-Ureylenebis[6-(9-hydroxy-7-sulfo-2H-naphtho[1,2-d]triazol-2-yl)benzenesulfonic acid] tetrasodium salt as aluminum lake, micronized | 0.05 – 5 (acid equivalent) |
| Polysorbate 80 USP | 0.2 |
| Polyethylene 3.0 | |
| Sodium Chloride USP | 0.8 |
| Benzyl Alcohol H.F. | 0.9 |
| HCl to pH 6 – 8 | qs |
| Water for injection qs ad | 100.0 |

The compounds of this invention may be administered internally, e.g., orally or parenterally, such as intra-articularly, to a warm-blooded animal to inhibit complement in the body fluid of the animal, such inhibitation being useful in the amelioration or prevention of those reactions dependent upon the function of complement, such inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg./kg./day, or every six hours for more rapidly excreted salts, may be used. For intra-articular use for large joints such as the knee, from about 2 to about 20 mg./joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg./kg. to about 100 mg./kg./ of body weight of animal per day. The usual daily dosage for a 70 kg. subject may vary from about 350 mg. to about 3.5 g. Unit doses of the compound can contain from about 0.5 mg. to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety for forms depending on the form of preparation desired for administration, i.e., oral or parenteral. The compounds can be used in compositions such as tablets. Here, the prinicpal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage, an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures or polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills powders packets, granules, wafers, cachets, teaspoonfuls, dropperfuls, ampules, vials, segregates multiples of any of the foregoing and other forms as herein described.

The complement inhibiting activity of a representative compound of this invention has been demonstrated by one or more of the following identified tests: (i) Test, Code 026 (C1 inhibitor). This test measures the ability of activated human C1 to destroy fluid phase human C2 in the presence of C4 and appropriate dilutions of the test compound. An active inhibitor protects C2 from C1 and C4; (ii) Test, Code 035 (C3–C9 inhibitor) — This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known component dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg./kg. is then reported, unless otherwise stated; (v) Forssman Shock Test — Lethal shock is produced in guinea pig by an i.v. injection of anti-Forssman antiserum and the harmonic mean death time of treated guinea pigs is compared with that of simultaneous controls; (vi) Complement Level Reduction Test — In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

Table I shows that the principal compound of the invention possesses significant anti-complement activity.

TABLE I

| Compound | Biological Activities | | | |
|---|---|---|---|---|
| | Assay Results | | | |
| | In Vitro | | In Vivo | |
| | 026* | 035 | Forsmann | % Reduction Complement |
| 3,3'-Ureylenebis[6-(9-hydroxy-sulfo-2H-naphtho[1,2-d]triazol-2-yl)benzenesulfonic acid] tetrasodium salt | +4** | +1 | 44,49 | 42 |

*Tests identified by code herein.
**4=Activity 4 wells, a serial dilution assay; higher well number indicates higher activity. The serial dilutions are two-fold.

We claim:
1. A compound selected from those of the formula:

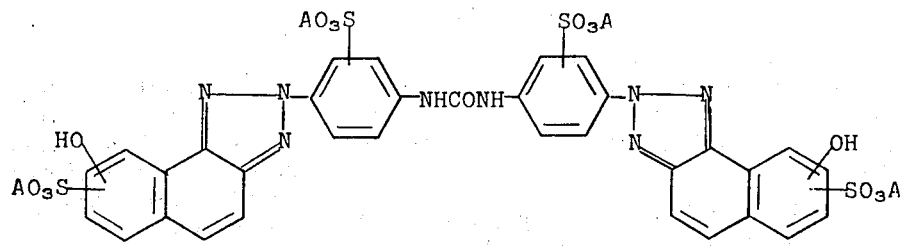

wherein A is H, Na or K, with the proviso that each A is identical in the same compound.

2. A compound selected from those of the formula:

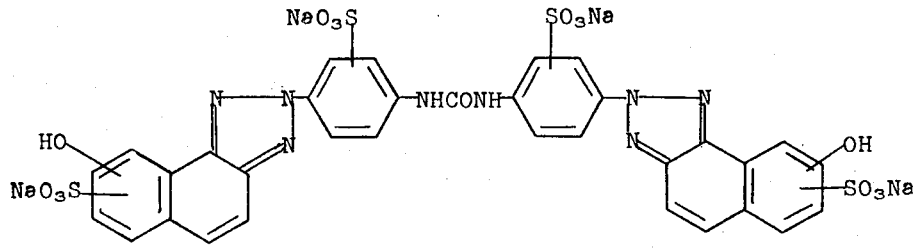

3. A compound according to claim 2, 3,3'-ureylenebis[6-(9-hydroxy-7-sulfo-2H-naphtho[1,2-d]triazol-2-yl)benzenesulfonic acid] tetrasodium salt of the formula:

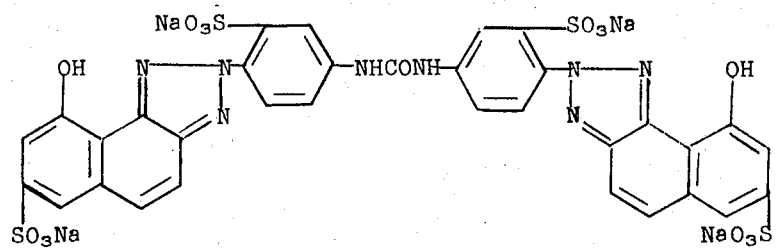

4. A method of inhibiting the complement system in a body fluid which comprises subjecting said body fluid to the action of an effective complement inhibiting amount of a compound of the formula:

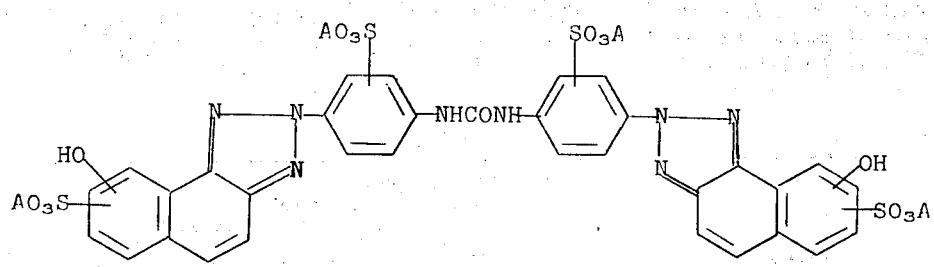

wherein A is H, Na or K, with the proviso that each A is identical in the same compound.

5. A method according to claim 4, wherein the compound is 3,3'-ureylenebis[6-(9-hydroxy-7-sulfo-2H-naphtho-[1,2-d]triazol-2-yl)benzenesulfonic acid] tetrasodium salt.

6. A method of inhibiting the complement system in a warm-blooded animal which comprises internally administering to said animal an effective complement inhibiting amount of a compound of the formula:

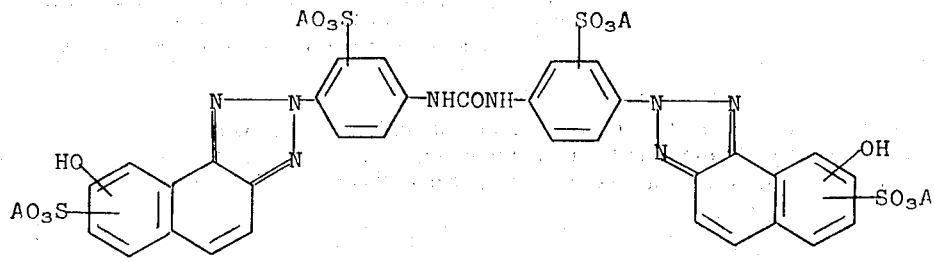

wherein A is H, Na or K, with the proviso that each A is identical in the same compound.

7. A method according to claim 6 wherein the compound is 3,3'-ureylenebis[6-(9-hydroxy-7-sulfo-2H-naphtho-[1,2-d]triazol-2-yl)benzenesulfonic acid] tetrasodium salt.

* * * * *